United States Patent
Klima

[11] Patent Number: 5,928,563
[45] Date of Patent: Jul. 27, 1999

[54] AGRICULTURAL ADJUVANT

[75] Inventor: Rudolph Klima, Lansdale, Pa.

[73] Assignee: Henkel Corporation, Gulph Mills, Pa.

[21] Appl. No.: 08/879,733

[22] Filed: Jun. 20, 1997

[51] Int. Cl.[6] .............................. B01F 3/00; A01N 25/02; A01N 25/30; C07G 3/00

[52] U.S. Cl. ........................ 252/364; 504/101; 504/116; 514/25; 514/54

[58] Field of Search ............................... 252/364; 514/25, 514/54; 504/116, 101; 536/18.6

[56] References Cited

U.S. PATENT DOCUMENTS

| | | | |
|---|---|---|---|
| 4,973,686 | 11/1990 | Kretschmann et al. | 536/118 |
| 5,049,192 | 9/1991 | Killick | 106/243 |
| 5,266,690 | 11/1993 | McCurry, Jr. et al. | 536/18.6 |
| 5,449,763 | 9/1995 | Wulff et al. | 536/18.6 |
| 5,516,747 | 5/1996 | Lachut | 504/116 |
| 5,550,115 | 8/1996 | Garst et al. | 514/25 |

*Primary Examiner*—Shean C. Wu
*Attorney, Agent, or Firm*—Ernest G. Szoke; Wayne C. Jaeschke; Steven J. Trzaska

[57] ABSTRACT

An adjuvant containing: (a) a sulfated alkyl oleate; (b) an alkyl polyglycoside corresponding to formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and (c) an alkyl ester.

18 Claims, No Drawings

AGRICULTURAL ADJUVANT

FIELD OF THE INVENTION

The present invention generally relates to agricultural adjuvants. More particularly, the invention relates to the use of sulfated alkyl oleate as either an agricultural adjuvant or an emulsifier for pesticide compositions.

BACKGROUND OF THE INVENTION

It is known that various pesticides such as insecticides, insect repellents, fungicides, bactericides, herbicides, and plant growth regulators may be formulated into various agricultural products for use on crops and ornamental plants, for controlling weeds, insects and the like. These products may be applied in the form of a liquid or a semi-solid dispersion.

The successful employment of any pesticide depends upon its proper formulation in a preparation that can be easily combined with water into ready-to-use form for application onto an agricultural substrate with safety to the applicator, animals and plants. The preparation and use of such formulations typically necessitates making them in concentrated form. Thus, the use of auxiliary agents such as solvents, emulsifiers, wetting and dispersing agents are typically required. The preparation of such pesticide concentrates, however, often times poses certain formulation problems due to the incompatibility of the pesticide component with other components combined therewith.

SUMMARY OF THE INVENTION

The present invention is directed to an adjuvant containing:

(a) a sulfated alkyl oleate;
(b) an alkyl polyglycoside corresponding to formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and (c) a $C_6$—$C_{18}$ alkyl ester.

The present invention is also directed to a pesticide composition containing:

(a) an adjuvant containing:
  (i) sulfated alkyl oleate;
  (ii) an alkyl polyglycoside corresponding to formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and (iii) a $C_6$—$C_{18}$ alkyl ester; and
(b) a biologically active ingredient.

The present invention is also directed to a process for treating a target substrate involving contacting the target substrate with a pesticide composition containing:

(a) an adjuvant containing:
  (i) a sulfated alkyl oleate;
  (ii) an alkyl polyglycoside corresponding to formula I:

$$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6; and (iii) a $C_6$—$C_{18}$ alkyl ester; and
(b) a biologically active ingredient.

DESCRIPTION OF THE INVENTION

Other than in the claims and in the operating examples, or where otherwise indicated, all numbers expressing quantities of ingredients or reaction conditions used herein are to be understood as being modified in all instances by the term "about".

The term target substrate, as used herein, means a plant, a plant pest, or a combination of a plant and a plant pest. A plant pest is defined as any living stage of any weed, insects, mites, nematodes, slugs, snails, protozoa, or other invertebrate animals, bacteria, fungi, other parasitic plants or reproductive parts thereof, viruses, or any organisms similar to or allied with any of the foregoing, or any infectious substances which can directly or indirectly injure or cause disease or damage in any plants or parts thereof, or any processed, manufactured, or other products of plants.

The adjuvant of the present invention is comprised of three primary components: (1) a sulfated alkyl oleate, (2) an alkyl polyglycoside, and (3) an alkyl ester. In the adjuvant form, it is difficult to effectively solubilize many adjuvant components at the high percentages necessary to form a concentrated product. Thus, if a high actives content of various organic liquid compounds is required to formulate an effective adjuvant concentrate containing components such as a methyl ester and an alkyl polyglycoside, it is imperative that the combined organic compounds be formed into a single phase, stable solution.

The sulfated alkyl oleate employed in the present invention is generally derived by the sulfation of an alkyl oleate. Suitable alkyl oleates for use in the present invention include those selected from the group consisting of methyl oleate, ethyl oleate, propyl oleate, butyl oleate, and mixtures thereof. The alkyl oleates may be derived either from the alcoholysis of olein or by the esterification of oleic acid with an alkanol. Once the alkyl oleate is formed, it is then sulfated.

The sulfation of organic compounds is well known in the art. There are primarily two types of reactions between an organic compound and sulfuric acid reactants: sulfation which produces sulfates having C—OS— linkages, and sulfonation which produce sulfonates having C—S linkages.

The sulfation process generally involves reacting the organic compound to be sulfated with either concentrated sulfuric acid/oleum, chlorosulfonic acid or sulfurtrioxide. The type of equipment and specific reaction conditions associated therewith which are employed to perform this process are well known in the art, an example of which is U.S. Pat. No. 4,973,686 issued to Henkel KGaA on Nov. 27, 1990, the entire contents of which is incorporated herein by reference.

A particularly preferred sulfated alkyl oleate for use in the present invention is a sulfated butyl oleate.

The alkyl polyglycosides which can be used in the invention correspond to formula I:

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, PLANTAREN® or AGRIMUL® surfactants from Henkel Corporation, Ambler, Pa., 19002. Examples of such surfactants include but are not limited to:

1. GLUCOPON® 220 Surfactant—an alkyl polyglycoside in which the alkyl group contains 8 to 10 carbon atoms and having an average degree of polymerization of 1.5.
2. GLUCOPON® 225 Surfactant—an alkyl polyglycoside in which the alkyl group contains 8 to 10 carbon atoms and having an average degree of polymerization of 1.7.
3. GLUCOPON® 600 Surfactant—an alkyl polyglycoside in which the alkyl group contains 12 to 16 carbon atoms and having an average degree of polymerization of 1.4.
4. GLUCOPON® 625 Surfactant—an alkyl polyglycoside in which the alkyl group contains 12 to 16 carbon atoms and having an average degree of polymerization of 1.4.
5. APG® 325 Surfactant—an alkyl polyglycoside in which the alkyl group contains 9 to 11 carbon atoms and having an average degree of polymerization of 1.6.
6. PLANTAREN® 2000 Surfactant—an alkyl polyglycoside in which the alkyl group contains 8 to 16 carbon atoms and having an average degree of polymerization of 1.4.
7. PLANTAREN® 1300 Surfactant—an alkyl polyglycoside in which the alkyl group contains 12 to 16 carbon atoms and having an average degree of polymerization of 1.6.
8. AGRIMUL® PG 2067 Surfactant—an alkyl polyglycoside in which the alkyl group contains 8 to 10 carbon atoms and having an average degree of polymerization of 1.7.
9. AGRIMUL® PG 2069 Surfactant—an alkyl polyglycoside in which the alkyl group contains 9 to 11 carbon atoms and having an average degree of polymerization of 1.6.

Other examples include alkyl polyglycoside surfactant compositions which are comprised of mixtures of compounds of formula I as described in U.S. Pat. Nos. 5,266,690 and 5,449,763, the entire contents of both of which are incorporated herein by reference.

A particularly preferred alkyl polyglycoside for use in the present invention is one corresponding to formula I wherein $R_1$ is a monovalent organic radical having from about 8 to about 16 carbon atoms, and preferably from about 8 to about 11 carbon atoms, b is zero, and a is a number having a value of from about 1.3 to about 1.8, and preferably from about 1.4 to about 1.7.

Suitable alkyl esters for use in the present invention comprise any of a group of fatty esters derived from coconut and other vegetable oils, tallow, and the like. The alkyl esters may generally be chosen from the group consisting of methyl esters, ethyl esters, propyl esters, butyl esters, and mixtures thereof. These compounds contain alkyl groups ranging from $C_8$—$C_{18}$ in varying percentages, i.e., having varying carbon chain length distributions. A particularly preferred alkyl ester is a $C_{8-18}$ methyl ester, and most preferably a methyl oleate.

According to one embodiment of the present invention, there is provided an adjuvant containing: (a) from about 5 to about 20% by weight, preferably from about 8 to about 15% by weight, and most preferably about 10% by weight, of a sulfated alkyl oleate, and preferably a sulfated butyl oleate, (b) from about 0.1 to about 15% by weight, preferably from about 5 to about 12% by weight, and most preferably about 10% by weight, of an alkyl polyglycoside, and (c) from about 0.1 to about 80% by weight, preferably from about 25 to about 80% by weight, and most preferably from about 50 to about 80% by weight, of an alkyl ester, preferably a methyl ester, and most preferably a methyl oleate, all weights being based on the weight of the emulsifier composition.

The adjuvant of the present invention, because it is comprised of three organic liquids, i.e., a sulfated alkyl oleate, an alkyl polyglycoside and an alkyl ester, form a mutually soluble mixture of organic liquids by the mechanism of co-solvency. The fat soluble alkyl ester, the water and fat soluble sulfated alkyl oleate and the partially fat soluble and water soluble alkyl polyglycoside, act as synergistic co-solvents to produce a mutually soluble adjuvant.

The adjuvant can accommodate, i.e., solubilize, biologically active ingredients possessing a wide range of solubility profiles ranging from oil soluble to water soluble. Thus, a stable pesticide composition comprising a mixture of the above-disclosed adjuvant and a biologically active ingredient can easily be formulated. Upon dilution of the pesticide composition, the alkyl polyglycoside and the sulfated alkyl oleate act as surfactants, by virtue of their molecules possessing both polar and non-polar portions and exhibiting critical micelle concentrations (CMC's). These surfactants stabilize emulsion particles which contain the biologically active ingredients. The biologically active ingredient is carried or spread across the target substrate by the mechanism of surface chemistry, i.e., low surface tension liquids or emulsions spread over higher surface tension target substrates.

According to another aspect of the present invention, there is provided a pesticide composition for use in treating target substrates such as those disclosed previously. The pesticide composition is generally comprised of the above-disclosed adjuvant concentrate and a biologically active ingredient. The pesticide composition of the present invention generally contains from about 0.01 to about 15% by weight, preferably from about 1 to about 10% by weight, and most preferably from about 2 to about 5% by weight, of a biologically active ingredient, and the remainder, the above-disclosed adjuvant.

The biologically-active ingredients used to make pesticide compositions according to the invention are generally selected from the group consisting of insecticides, insect repellents, fungicides, bactericides, bacteriostats, herbicides, and plant growth regulators, all of which are based on biologically-active ingredients. Suitable insecticides include, for example, O,O-diethyl O-(2-isopropyl-4-methyl-6-pyrimidinyl)phosphorothioate, O,O-diethyl S-2-[(ethylthio)ethyl]phosphorodithioate, O,O-dimethyl O-(3-methyl-4-nitrophenyl)thiophosphate, O,O-dimethyl S-(N- methylcarbamoylmethyl)phosphorodithioate, O,O-dimethyl-S-(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphosphonate, O,O-diethyl-O-(5-phenyl-3-isooxazolyl)phosphorothioate, O,O-dimethyl O-(2,5-dichloro-4-bromophenyl)phosphorothioate, O,O-dimethyl-O-)3-methyl-4-methylmercaptophenyl) thiophosphate, O-ethyl O-p-cyanophenyl-O-phenylphosphorothioate, O,O-dimethyl-S-(1,2-dicarboethoxyethyl) phosphorodithioate, 2-chloro-(2,4,5-trichlorophenyl)vinyldimethyl phosphate, 2-chloro-1-(2,4-dichlorophenyl)vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphorodithioate, S-[(6-chloro-2-oxo-3-benzooxazolinyl)methyl]O,O-diethyl phosphorodithioate, 2-chloro-1-(2,4-dichlorophenyl)vinyl diethylphosphate O,O-diethyl O-(3-oxo-2-phenyl-2H-pyridazine-6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl 2,2,2-trichloroethanol, 2-(p-tert-butyl-phenoxy)isopropyl-2'-chloroethylsulfite, azoxybenzene, di-(p-chlorophenyl)-cyclopropyl carbinol, di[tri(2,2-dimethyl-2-phenylethyl)tin] oxide, 1-(4-chlorophenyl)-3-(2,6-difluorobenzoyl)urea and S-tricyclohexyltin O,O-diisopropylphosphorodithioate; 2-methyl-2-(methylthio)propionaldehyde O-(methylcarbamoyl)oxime; ethyl [2-(4-phenoxyphenoxy) ethyl] carbamate; butyl-2,3-dihydro-2,2-dimethylbenzofuran-7-yl N,N'-dimethyl-N,N'-thiodicarbamate; 1-naphthyl methyl carbamate; 2-(ethylthiomethyl)phenyl methylcarbamate; 5-(4-phenoxybutyl)dimethylthiocarbamate; dimethyl N,N'-(thiobis(methylimino)carbonyloxy)-bis(ethanimidothioate); (RS)-α-cyano-3-phenoxybenzyl-(RS)-2-(4-chlorophenyl)-3-methylbutyrate; (RS)-α-cyano-3-phenoxyphenyl-(RS)-2,2-dichloro-1-(4-ethoxyphenyl)cyclopropanecarboxylate; (RS)-α-cyano-3-phenoxybenzyl-N-(2-chloro-α,α,α-trifluoro-p-tolyl-D-valinate; 3-phenoxybenzyl-(1RS)-cis, trans-3-(2,2-dichlorovinyl)-2,2-dimethylcyclopropanedicarboxylate.

Insect repellents which may be employed include but are not limited to 2-ethyl-1,3-hexanediol; N-octyl bicycloheptene dicarboximide; N,N-diethyl-M-toluamide; 2,3:4,5-Bis (2-butylene) tetrahydro-2-furaldehyde; Di-n-propyl isocinchomeronate; and 2-hydroxyethyl-n-octyl sulfide.

Fungicides which may be employed include but are not limited to 3,3'-ethylenebis (tetrahydro-4,6-dimethyl-2H-1,3,5-thiadiazine-2-thione), zinc or manganese ethylenebis (dithiocarbamate), bis-(dimethyldithiocarbamoyl)disulfide, zinc propylenebis (dithiocarbamate), bis (dimethyldithiocarbamoyl) ethylenediamine; nickel dimethyldithiocarbamate, methyl-1(butylcarbamoyl)-2-benzimidazolecarbamate, 1,2-bis(3-methoxycarbonyl-2-thioureido)benzene, 1-isopropylcarbamoyl-3-(3,5-dichlorophenyl)hydantoin, potassium N-hydroxymethyl-N-methyldithiocarbamate and 5-methyl-10-butoxycarbonylamino-10, 11-dehydrodibenzo (b,f)azepine; pyridine fungicides such as zinc bis(1-hydroxy-2(1H) pyridinethionate and 2-pyridinethiol-1-oxide sodium salt; O,O-diisopropyl S-benzylphosphorothioate and O-ethyl S,S-diphenyldithiophosphate; phthalimide fungicides such as N-(2,6-p-diethylphenyl)phthalimide and N-(2,6-diethylphenyl)-4-methylphthalimide; dicarboxyimide fungicides such as N-trichloromethylthio 4-cyclohexene-1,2-dicarboxyimide and N-tetrachloroethylthio-4-cyclohexene-1,2-dicarboxyimide; 5,6-dihydro-2-methyl-1,4-oxathine-3-carboxanilido-4,4-dio xide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate, pentachloronitrobenzene; 1,4-dichloro-2,5-dimethoxybenzene; 5-methyl-s-triazol-(3,4-b)benzthiazole; 2-(thiocyanomethylthio)benzothiazole; 3-hydroxy-5-methylisooxazole; N-2,3-dichlorophenyltetrachlorophthalamic acid; 5-ethoxy-3-trichloromethyl-1,2,4-thiaziazole; 2,4-dichloro-6-(0-chloroanilino)-1,3,5-triazine; 2,3-dicyano-1,4-dithioanthraquinone; copper 8-quinolinate; polyoxine; validamycin; cycloheximide; iron methanearsonate; diisopropyl 1,3-dithiolane-2-iridene malonate; 3-allyloxy-1,2-benzoisothiazol-1,1-dioxide; kasugamycin; Blasticidin S; 4,5,6,7-tetrachlorophthalide; 3-(3,5-dichlorophenyl)5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonyl imidate; 4-chlorophenoxy-3,3-dimethyl-1-(1H,1,3,4-triazol-1-yl)-2-butanone; methyl-D, L-N-(2,6-dimethylphenyl)-N-(2'-methoxyacetyl) alaninate; N-propyl-N-[2-(2,4,6-trichlorophenoxy)ethyl]imidazol-1-carboxamide; N-(3,5-dichlorophenyl)succinamide; tetrachloroisophthalonitrile; 2-dimethylamino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolol-[3,2,1-i,j]quinoline-2-one; 3'-isopropoxy-2-methylbenzanilide; 1-[2-(2,4-dichlorophenyl)-4-ethyl-1,3-dioxorane-2-methyl]-1H,1,2,4-triazol; 1,2-benzisothiazoline-3-one; basic copper chloride; basic copper sulfate; N'-dichlorofluoromethylthio-N,N-dimethyl-N-phenyl sulfamide; ethyl-N-(3-dimethylaminopropyl) thiocarbamate hydrochloride; piomycin; S,S-6-methylquinoxaline-2,3-di-yldithiocarbonate; complex of zinc and manneb; di-zinc bis(dimethyldithiocarbamate) ethylenebis (dithiocarbamate).

Plant growth regulators which may be employed include but are not limited to N-methoxycaronyl-N'-4-methylphenylcarbamoylethylisourea and 1-(4-chlorophenylcarbamoyl)-3-ethoxycarbonyl-2-methylisourea; another type of plant growth regulators such as sodium naphthaleneacetate, 1,2-dihydropyridazine-3,6-dione and gibberellins; traizine herbicides such as 2-methylthio-4,6-bisethylamino-1,3,5-triazine, 2-chloro-4,6-bisethylamino-1,3,5-triazine, 2-methoxy-4-ethylamino-6-isopropylamino-1,3,5-triazine, 2-chloro-4-ethylamino-6-isopropylamino-s-triazine, 2-methylthio-4,6-bis (isopropylamino)-S-triazine and 2-methylthio-4-ethylamino-6-isopropylamino-s-triazine; phenoxy herbicides such as 2,4-dichlorophenoxyacetic acid and methyl, ethyl, and butyl esters thereof. 2-chloro-4-methylphenoxyacetic acid, 4-chloro-2-methylphenoxyacetic acid and ethyl 2-methyl-4-chlorophenoxybutylate; diphenylether herbicides such as 2,4,6-trichlorophenyl-4'-nitrophenylether,2,4-dichlorophe nyl-4'- nitrophenylether and 3,5-dimethylphenyl-4'-nitrophenylether; urea herbicides such as 3-(3,4-dichlorophenyl)-1-methoxy-1-methyl urea, 3-(3,4-dichlorophenyl)-1,1-dimethylurea and 3-(4-chlorophenyl)-1,1-dimethyl urea; carbamate herbicides such as 3-methoxycarbonylaminophenyl-N-(3-methylphenyl) carbamate, isopropyl-N-(3-chlorophenyl)carbamate and methyl-N-(3,4'-dichlorophenyl)carbamate; uracil herbicides such as 5-bromo-3-sec-butyl-6-methyluracil and 1-cyclohexyl-3,5-propyleneuracil; thiolcarbamate herbicides such as S-(4-chlorobenzyl)-N,N- diethylthiolcarbamate,S-ethyl-N-cyclohexyl-N-ethylthiolcarbamate and S-ethyl-hexahydro-1H-azepine-1-carbothioate and S-ethyl-N,N-di-n-propyl-thiocarbamate; pyridinium herbicides such as 1,1'-di-methyl-4,4'-bispyridinium dichloride; phosphoric herbicides such as N-(phosphonomethyl)glycine; aniline herbicides such as alpha-trifluoro-2,6-dinitro-N,N-dipropyl-p-toluidine, 4-(methylsulfonyl)-2,6-dinitro-N,N-dipropylaniline and N[3], N[3]-diethyl-2,4-dinitro-6-trifluoromethyl-1,3-phenylene diamine; acid anilide herbicides such as 2-chloro-2',6'-diethyl-N-(butoxymethyl)acetoanilide, 2-chloro-2',6'-diethyl-N-(methoxymethyl)acetoanilide, and 3,4-dichloropropioneanilide; pyrazole herbicides such as 1,3-dimethyl-4-(2,4-dichlorobenzoyl)-5-hydroxypyrazole and 1,3-di-methyl-4-(2,4-dichlorobenzoyl)-5-(p-toluenesulfonyloxy)pyrazole; 5-tert-butyl-3-(2,4-dichloro-5-isopropoxyphenyl)-1,3,4-oxadiazoline-2-one; 2-[N-isopropyl,N-(4-chlorophenyl)carbamoyl]-4-chloro-5-methyl-4-isooxazoline-3-one; 3-isopropylbenzo-2-thia-1,3-diazinone-(4)-2,4-dioxide and 3-(2-methyl-phenoxy) pyridazine.

The precise amount of adjuvant and biologically active ingredient used to formulate the pesticide composition will depend upon the specific application itself, i.e., the target substrate to be treated, the area to be treated, etc. The same holds true with respect to the amount of water used to dilute a particular pesticide composition when forming a ready-to-use aqueous pesticide composition. Thus, it is within the skill of the applicator to determine the specific amount of active ingredient to be used in a particular application. In general, however, a ready-to-use aqueous pesticide composition will typically contain from about 0.1 to about 20% by weight, preferably from about 1 to about 15% by weight, and most preferably from about 5 to about 10% by weight, of the above-disclosed pesticide composition, and remainder, water.

According to yet another aspect of the present invention, there is provided a process for treating a target substrate involving contacting the substrate with the above-disclosed aqueous pesticide composition. The pesticide composition may be applied by aerial spraying, by in seed row application, with a fertilizer or the like.

It should be noted that additional solvents, emulsifiers and adjuvants may be used by the applicator, if desired. It is thus within the skill of the applicator to determine if, and in what amounts, additional ingredients will be employed.

The present invention will be better understood from the examples which follow, all of which are intended for illustrative purposes only, and are not meant to limit the scope of the invention in any way.

EXAMPLES

Adjuvant concentrates were formed, each of which contained 20% by weight methyl laurate as the methyl ester. The concentrates were then tested to determine their solubility. Their formulations and test results are found in Table 1, below.

TABLE 1

| Example | Sulfated butyl oleate | AGRIMUL ® (% w/w) | Bottom Layer (in.) | Middle Layer (in.) | Top Layer (inches) |
|---|---|---|---|---|---|
| 1 | 100 | 0 | single phase | — | — |
| 2 | 50 | 50 | single phase | — | — |
| 3 | 25 | 75 | 0.62 | 1.0 | 1.12 |
| 4 | 0 | 100 | 0.12 | 0.56 | 2.0 |
| 5 | 0 | 100 | 0.12 | 0.56 | 2.0 |
| 6 | 40 | 60 | 2.0 | 0 | 0.67 |
| 7 | 30 | 70 | 0.94 | 0 | 2.0 |
| 8 | 35 | 65 | 1.0 | 0 | 1.8 |
| 9 | 50 | 50 | single phase | — | — |

AGRIMUL ® PG 2069 is an alkyl polyglycoside in which the alkyl group contains 9 to 11 carbon atoms, and has a degree of polymerization of 1.6.

As can be seen from the data above, the use of sulfated butyl oleate, in combination with an alkyl polyglycoside and a methyl ester, allows for the formulation of an adjuvant concentrate which is completely solubilized into a single phase. Moreover, Examples 1 and 2 remained stable, i.e., in a single phase, after more than 1 week of storage.

What is claimed is:

1. A adjuvant comprising:
   (a) a sulfated alkyl oleate;
   (b) an alkyl polyglycoside corresponding to formula I:

$$R_1O(R_2O)_b(Z)_a \qquad \text{I}$$

wherein $R_1$ is a monovalent organic radical having from about 8 to about 16 carbon atoms; $R_2$ is a divalent alkylene radical having from 2 to 4 carbon atoms; Z is a saccharide residue having 5 or 6 carbon atoms; b is 0; a is a number having a value of from about 1.3 to about 1.8; and
   (c) an alkyl ester.

2. The adjuvant of claim 1 wherein the sulfated alkyl oleate is sulfated butyl oleate.

3. The adjuvant of claim 1 wherein the sulfated alkyl oleate is present in the concentrate in an amount of from about 5 to about 20% by weight, based on the weight of the adjuvant.

4. The adjuvant of claim 1 wherein the alkyl polyglycoside is present in the adjuvant in an amount of from about 0.1 to about 15% by weight, based on the weight of the adjuvant.

5. The adjuvant of claim 1 wherein the alkyl ester is a $C_6$—$C_{18}$ methyl ester.

6. The adjuvant of claim 5 wherein the methyl ester is methyl laurate.

7. The adjuvant of claim 1 wherein the alkyl ester is present in the adjuvant in an amount of from about 0.1 to about 80% by weight, based on the weight of the adjuvant.

8. An adjuvant comprising:
   (a) from about 8 to about 15% by weight of a sulfated butyl oleate;
   (b) from about 5 to about 12% by weight of an alkyl polyglycoside corresponding to formula I:

$$R_1O(R_2O)_b(Z)_a \qquad \text{I}$$

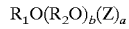

wherein $R_1$ is a monovalent organic radical having from about 8 to about 16 carbon atoms; $R_2$ is a divalent alkylene radical having from 2 to 4 carbon atoms; Z is a saccharide residue having 5 or 6 carbon atoms; b is zero; a is a number having a value of from about 1.3 to about 1.8; and
   (c) from about 25 to about 80% by weight of a methyl laurate, all weights being based on the weight of the adjuvant.

9. The composition of claim 8 wherein the biologically active ingredient is present in the composition in an amount of from about 0.01 to about 15% by weight, based on the weight of the composition.

10. A pesticide composition comprising:
   (a) an adjuvant containing:
      (i) a sulfated alkyl oleate;
      (ii) an alkyl polyglycoside corresponding to formula I:

$$R_1O(R_2O)_b(Z)_a \qquad\qquad I$$

wherein $R_1$ is a monovalent organic radical having from about 8 to about 16 carbon atoms; $R_2$ is a divalent alkylene radical having from 2 to 4 carbon atoms; Z is a saccharide residue having 5 or 6 carbon atoms; b is 0; a is a number having a value from about 1.3 to about 1.8; and
      (iii) an alkyl ester; and
   (b) a biologically active ingredient.

11. The composition of claim 10 wherein the sulfated alkyl oleate is sulfated butyl oleate.

12. The composition of claim 10 wherein the sulfated alkyl oleate is present in the adjuvant in an amount of from about 5 to about 20% by weight, based on the weight of the adjuvant.

13. The composition of claim 10 wherein the alkyl polyglycoside is present in the adjuvant in an amount of from about 0.1 to about 15% by weight, based on the weight of the concentrate.

14. The composition of claim 10 wherein the alkyl ester is a $C_6$—$C_{18}$ methyl ester.

15. The composition of claim 14 wherein the methyl ester is methyl laurate.

16. The composition of claim 10 wherein the alkyl ester is present in the adjuvant in an amount of from about 0.1 to about 80% by weight, based on the weight of the concentrate.

17. An aqueous pesticide composition comprising:
   (a) from about 1 to about 15% by weight of the pesticide composition of claim 10; and
   (b) remainder, water, all weights being based on the weight of the composition.

18. A process for treating a target substrate comprising contacting the substrate with the aqueous pesticide composition of claim 17.

* * * * *